(12) United States Patent
Liu et al.

(10) Patent No.: US 9,693,886 B2
(45) Date of Patent: Jul. 4, 2017

(54) SHORT SHEATH DELIVERY SYSTEM FOR BILIARY METAL STENT VIA ENDOSCOPE

(71) Applicant: HARBIN MEDICAL UNIVERSITY, Harbin (CN)

(72) Inventors: Bingrong Liu, Harbin (CN); Bing Du, Harbin (CN); Zhonghong Liu, Harbin (CN); Shizhu Jin, Harbin (CN)

(73) Assignee: HARBIN MEDICAL UNIVERSITY, Harbin (CN)

( * ) Notice: Subject to any disclaimer, the term of this patent is extended or adjusted under 35 U.S.C. 154(b) by 90 days.

(21) Appl. No.: 14/967,586

(22) Filed: Dec. 14, 2015

(65) Prior Publication Data

US 2016/0166415 A1    Jun. 16, 2016

(30) Foreign Application Priority Data

Dec. 15, 2014 (CN) .......................... 2014 1 0777443

(51) Int. Cl.
*A61F 2/966* (2013.01)
*A61F 2/04* (2013.01)
*A61F 2/95* (2013.01)

(52) U.S. Cl.
CPC ........ *A61F 2/966* (2013.01); *A61F 2002/041* (2013.01); *A61F 2002/9517* (2013.01); *A61F 2002/9522* (2013.01)

(58) Field of Classification Search
CPC .... A61F 2/966; A61F 2002/9665; A61F 2/95; A61F 2002/9522
See application file for complete search history.

(56) References Cited

U.S. PATENT DOCUMENTS

2004/0143272 A1* 7/2004 Cully .................. A61F 2/95
606/108
2014/0135894 A1  5/2014 Norris et al.

FOREIGN PATENT DOCUMENTS

CN          103142336          6/2013

OTHER PUBLICATIONS

Chinese Search Report filed in CN 201410777443.1 dated May 15, 2015.

* cited by examiner

*Primary Examiner* — Katrina Stransky
*Assistant Examiner* — Daniel Bissing
(74) *Attorney, Agent, or Firm* — Rankin, Hill & Clark LLP (57) ABSTRACT

A short sheath delivery system comprises a delivery device for a stent and a fixing device. A delivery device is used for delivering a stent part on a stricture lesion via an endoscope along a guidewire; the fixing device is used for fixing the delivery device on an endoscope biopsy port. The delivery device comprises a tip, an inner rod, a secondary rod, a main rod, a sliding rod, a trailing end, a guidewire cavity, an injection tube, a stent, a short sheath, a connection thread and a handle; the stent is preloaded in an empty cavity formed by the inner rod and the short sheath; the length of the short sheath is longer than that of the stent, and is less than that of the secondary rod; the external diameter of the secondary rod is less than the inner diameter of the short sheath, and the external diameter of the main rod is equal to or greater than that of the short sheath; the handle is sleeved around the sliding rod; and the handle is connected with the short sheath by the connection thread.

7 Claims, 6 Drawing Sheets

SHORT SHEATH DELIVERY SYSTEM FOR BILIARY METAL STENT VIA ENDOSCOPE

TECHNICAL FIELD

The present invention relates to a method of delivering a biliary stent via an endoscope and, more particularly, to a short sheath delivery system for a biliary metal stent via an endoscope.

BACKGROUND

In recent years, placing metal stents into biliary duct via the endoscope has been an important method of treatment of many malignant biliary strictures. Existing biliary metal stent delivery system contains a long outer sheath and an inner rod, the stent is preloaded in the cavity between the outer sheath and the inner rod. In the process of delivering a stent, it is essential to ensure that the inner rod and the stent are in the predetermined position relative to the stricture region while withdrawing the outer sheath. For neither the sheath nor the inner rod is fixed relative to the region of deploying the stent, it is required for the operator to closely cooperate with the assistant to control the relative movement of the inner rod and the sheath to maintain the stent without migration. Because the long outer sheath suffers friction of the operating channel of the endoscope, when the assistant pulling back the sheath, the operator needs to pull out the sheath from the operating channel at the same speed, otherwise it will cause the stent deviates from the predetermined site due to a relative motion moving the inner rod forward. Therefore, it is difficult to operate existing metal stent delivery devices. In this process, any slight mistake will deviate or even fall off the deployed the stent, and will even result in a surgical failure. Therefore, there is a need to reload the stent into the sheath and re-deploy the stent for the accurate stent positioning.

Therefore, they are demanding problems to be solved in the art: how to carry out a single-person operation, and how to simply and precisely deploy the stent to the target position after accurately locating the stent's position.

SUMMARY OF THE INVENTION

In order to achieve the objects above, the present invention provides a short sheath delivery system for a biliary metal stent via an endoscope, wherein the short sheath delivery system is formed by a delivery device and a fixing device, in order to deploy it simply and precisely to the target position after locating the stent's position. And the delivery system implements a single-hand operation, reduces an operative difficulty index, and improves an operational success ratio.

The present invention provides a short sheath delivery system for a biliary metal stent via an endoscope. The delivery system comprises a delivery device and fixing device.

The delivery system comprises successively with a tip, an inner rod, a secondary rod, a main rod, a sliding rod and a trailing end, a short sheath, a handle and a stent, wherein the short sheath and the handle are connected by a connection thread, and the stent is arranged around the inner rod, wherein, There are a guidewire inlet and an injection tube outlet on a top of the tip;

The tip, the inner rod, the secondary rod and the main rod are integrated, and the external diameter of the inner rod is less than that of the secondary rod, and the external diameter of the secondary rod is less than that of the main rod;

The short sheath covers around the inner rod, and an empty cavity is formed between the short sheath and the inner rod so as to contain the stent in the empty cavity before the stent is deployed;

The length of the short sheath is greater than that of the stent, and is less than that of the secondary rod;

The external diameter of the secondary rod is less than the inner diameter of the short sheath, and T-shaped longitudinal sliding grooves are arranged on two sides of an interior of the secondary rod, and T-shaped buckles are arranged at a tail of the short sheath and are embedded in the T-shaped longitudinal sliding grooves, wherein one end of the connection thread is connected with a thread attachment point of the T-shaped buckle, wherein the thread attachment point of the T-shaped buckle is arranged on one of the T-shaped buckles;

The external diameter of the main rod is equal to or greater than that of the short sheath;

A long cylindrical channel extends from the guidewire inlet arranged at the tip to the trailing end and goes successively through the tip, the inner rod, the secondary rod, and the main rod to a guidewire outlet arranged on the main rod, wherein the long cylindrical channel is a guidewire cavity; and the guidewire outlet is arranged on a side wall of the main rod, and the guidewire outlet is an intersection point of the tube wall of the main rod and the guidewire cavity when the guidewire cavity extends out from the main rod;

The external diameter of the sliding rod is greater than that of the main rod; concave slideways are arranged on two sides of the sliding rod, and the handle is sleeved around the sliding rod; and convex protrusions are arranged on inner sides of the handle and protrude to concave sides of the concave slideways so as to slide the handle along the sliding rod; thread attachment points of the convex protrusion are arranged on a top of the convex protrusions so as to be connected with the other end of the connection thread;

The connection thread starts at the T-shaped buckles arranged at a tail part of the short sheath, successively passes through the T-shaped longitudinal sliding grooves which are arranged on the two sides of the interior of the secondary rod, through a connection thread tube which is arranged in the main rod, then through a main rod thread outlet which is arranged on a tube wall at a tail part of the main rod, and through a thread passing hole of the sliding rod which is arranged on a top of the sliding rod, and finally connects to the thread attachment points of the convex protrusion, therefore the connection thread drives the short sheath to slide along the secondary rod towards the trailing end when the handle slides along the sliding rod to the trailing end;

An injection port is arranged at the trailing end so as to be externally connected with a syringe needle;

An injection tube is arranged from the injection tube outlet which is located at the tip, through the tip, the inner rod, the secondary rod, the main rod, the sliding rod, and to the injection port which is located at the trailing end; the injection tube is used for injecting a contrast agent through the injection port, so as to locate the position of the tip by discharging the contrast agent from the injection tube outlet.

Wherein, the length of the sliding rod is not less than that of the secondary rod.

Wherein, X-ray opaque markers are coated at two ends of the inner rod to locate positions of the inner rod and the stent by X-ray.

Wherein, the fixing device is used for connecting the endoscope biopsy port and fixing the main rod and the guidewire, wherein, the fixing device including a fixing cap and a fixing latch, wherein, A retractable biopsy channel is arranged at the center of fixing cap so as to sleeve the delivery device on the endoscope biopsy port; a thin adhesive film is arranged annuarly in a middle part of the retractable biopsy channel, and the thin adhesive film has good resilience and sealability so as to prevent gases and contents in the retractable biopsy channel from counterflowing; and the thin adhesive film would be punctured in a middle part of the thin adhesive film when the main rod and the guidewire of the delivery device pass through the retractable biopsy channel; a wedge-shaped guidewire groove is arranged longitudinally from the exterior of the pass channel to the top of the thin adhesive film so as to fix the guidewire piercing out from the guidewire outlet; a base groove to connect the endoscope biopsy port and an annular rubber ring to clamp the endoscope biopsy port are both arranged at the bottom of the fixing cap;

The fixing latch includes a U-shaped groove, a pulling latch and a latch ring, wherein the U-shaped groove and the pulling latch are respectively fixed on two sides of the guidewire groove, and the pulling latch can be turned over by the main shaft, the latch ring is a rectangular hollow ring, wherein one side of the latch ring is embedded in side shaft holes of two sides of the pulling latch and drives the pulling latch to turn over along with the main shaft, and turn over the pulling latch and the latch ring so as to turn over the pulling latch back to clamp the fixing latch tightly after the latch ring latches the U-shape groove, therefore the retractable channel retracts to fix the main rod and to press and fix the guidewire tightly by the guidewire groove.

Wherein the fixing latch and the fixing cap are integrated.

The present invention also provides a single-handed operating method of the short sheath delivery device or the delivery system for delivering the metal stent in the biliary tract via the endoscope, wherein the method comprises the following steps: a thumb pressing against the trailing end, at least two fingers pulling two sides of the handle respectively to slowly move close to the thumb, and the handle driving the short sheath to move over the secondary rod by the connection thread, therefore the stent loses an external pressure around and expands to be deployed.

Compared with the prior art, the beneficial effect of the present invention is in that:

The present invention provides a short sheath delivery system for a biliary metal stent via an endoscope. Traditionally, the sheath covered the stent delivery device all through; however, in the present invention, the short sheath is only slightly longer than the stent. Traditionally, the delivery device has only one tube; however, in the present invention, the delivery device is divided into a main rod and a secondary rod, wherein the fixing device fixes the main rod, and the short sheath is shorter than the secondary rod and can be coated on the secondary rod. In the present invention, when the stent is deployed, outside the patient's body, the delivery device is fixed in the biopsy hole of the endoscope by the fixing device, and the locations of the delivery device and the inner rod are kept constant. In the present invention, the short sheath retreats from the stent backwardly enough when the operator pulls out the handle by one single hand. In the present invention, because the sheath is shorter, it will not move the stent during retreating the inner rod and the stent, until the stent is deployed completely and accurately, therefore it becomes a simple, accurate, safe and single-person operation to delivery the stent.

DESCRIPTION OF THE DRAWINGS

In order to clearly illustrate the embodiments of the present invention or the implementations of the prior art, the accompanying drawings for the present invention or the prior art are described as follows briefly. Obviously, the given accompanying drawings are only embodiments of the present invention, therefore, those skilled in the art could get other drawings in accordance with the accompanying drawings without devoting a creative effort.

FIG. 2A1 is a cross-sectional view of the stent and the inner rod surrounded by the short sheath of an embodiment according to the present invention before the stent is deployed;

FIG. 2A2 is a cross-sectional view of the secondary rod and the tail part of the short sheath of an embodiment according to the present invention before the stent is deployed, wherein the tail part of the short sheath sleeves the secondary rod;

FIG. 2A3 is a cross-sectional view of the secondary rod of an embodiment according to the present invention before the stent is deployed;

FIG. 2A4 is a cross-sectional view with a guidewire cavity on the top side of the main rod of an embodiment according to the present invention before the stent is deployed;

FIG. 2A5 is a cross-sectional view without a guidewire cavity of the tail side of the main rod of an embodiment according to the present invention before the stent is deployed;

FIG. 2A6 is a cross-sectional view of the handle and the sliding rod of an embodiment according to the present invention before the stent is deployed, wherein the handle sleeves the sliding rod;

FIG. 2A7 is a cross-sectional view of the sliding rod of an embodiment according to the present invention before the stent is deployed;

FIG. 2B1 is a cross-sectional view of the stent and the inner rod of the delivery device of an embodiment according to the present invention after the stent is deployed;

FIG. 2B2 is a cross-sectional view of the short sheath and the secondary rod of the delivery device of an embodiment according to the present invention after the stent is deployed, wherein the short sheath sleeves the secondary rod;

Wherein, the above accompanying drawings are schematic for the structure, and the dimensions of different drawings are different from proportions of the actual objects, and their definite dimension relationship should refer to the written description of the specification.

Reference signs of drawings: 1—tip; 2—inner rod; 3—secondary rod; 4—main rod; 5—sliding rod; 6—trailing end; 7—short sheath; 8—connection thread; 9—handle; 10—stent; 11—guidewire inlet; 12—injection tube outlet; 13—guidewire cavity; 14—injection tube; 15—X-ray opaque marker; 16—T-shaped buckle; 17—thread attachment point of the T-shaped buckles; 18—T-shaped longitudinal sliding groove; 19—boundary of main rod and secondary rod; 20—guidewire outlet; 21—connection thread tube; 22—main rod thread outlet; 23—thread passing hole of the sliding rod; 24—concave slideways; 25—convex protrusion; 26—thread attachment point of the convex protrusion; 27—injection tube inlet; 28—injection port; 29—fixing cap; 30—retractable biopsy channel; 31—base groove; 32—annular rubber ring; 33—thin adhesive film; 34—guidewire groove; 35—pulling latch; 36—main shaft; 37—side shaft hole; 38—latch ring; 39—U-shaped groove; 40—endoscope; 41—endoscope biopsy port; 42—guidewire.

DETAILED DESCRIPTION OF THE EMBODIMENTS

With reference to the accompanying drawings in the embodiments of the present invention, the description of the technical solution of embodiments of the present invention is given clearly and integral as following. The given implementations are only part of the implementations according to the present invention obviously, but not entire implementations. Based on the embodiments of the present invention, all of the other implementations which get without devoting a creative effort by those skilled in the art should be deemed to be within the scope of the present invention.

The present invention provides a short sheath delivery system for a biliary metal stent via an endoscope, wherein the short sheath delivery system comprises delivery device and fixing device, wherein the delivery device is applied to carry the stent and send it into the biliary tract to placed it in the biliary tract via an endoscope, and after it arrives at the exact location of the biliary tract to be placed, an operator with single-handed pull back the handle which led to shift up the short sheath around the stent to deploy the stent; the fixing device is applied to fix the main rod, which is in the delivery device inserted in the fixing cap, at the endoscope biopsy port.

Figure 1A:
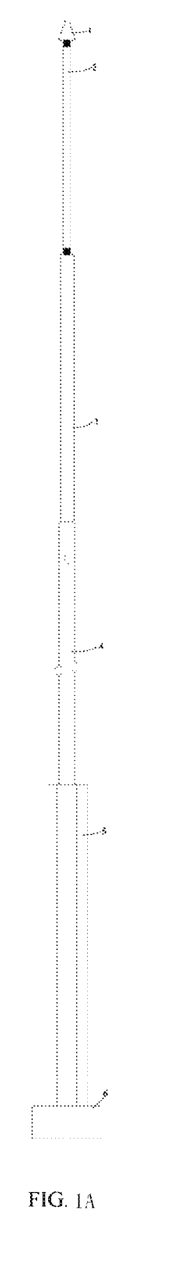
FIG. 1A is a schematic diagram of the main body of the delivery device of an embodiment according to the present invention, wherein the delivery device is formed by a tip, an inner rod, a secondary rod, a main rod, a sliding rod and a trailing end.
Figure 1B:
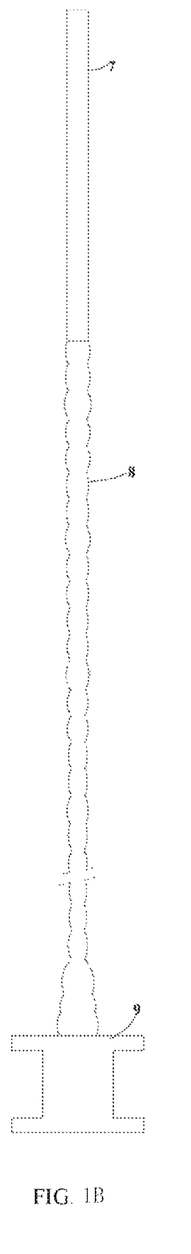
FIG. 1B is a schematic diagram of the delivery device of an embodiment according to the present invention, wherein the short sheath is connected with the handle by the connection thread.
Figure 1C:
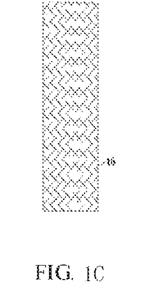
FIG. 1C is a side view of the stent to be pushed by the delivery device of an embodiment according to the present invention.

Please refer to FIG. 1A-FIG. 1C, which is the disintegrating schematic diagram of the main form of each structure of the delivery device of an embodiment according to the present invention. As shown in FIG. 1A-FIG. 1C, the delivery device comprises main part, sleeve system and stent 10, wherein as shown in FIG. 1A, the main part comprises tip 1, inner rod 2, secondary rod 3, main rod 4, sliding rod 5 and trailing end 6. As shown in FIG. 1B, the outer thimble system comprises the short sheath 7, the connection thread 8, and the handle 9. The handle 9 is preferably an H-shaped ring. The short sheath 7 and the handle 9 are jointed by the connection thread 8. FIG. 1C is a side view of stent 10 in the expanded state after it is deployed. Before the implementation of the operation, stent 10 has been compressed and wrapped inner rod 2 wrapped by short sheath 7, and the handle sleeves out of the sliding rod 5.

Figure 2A:
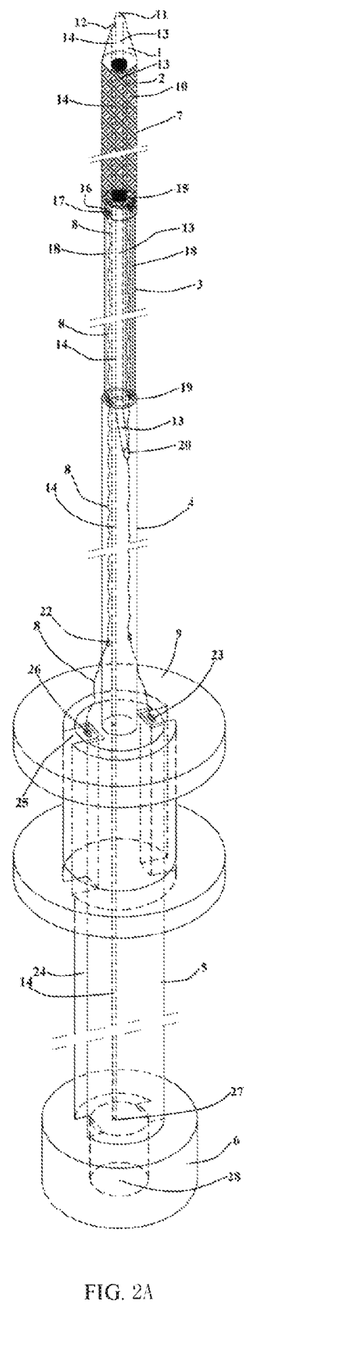
FIG. 2A is a structure diagram of the stent of the delivery device of an embodiment according to the present invention before the stent is deployed.
Figure 2A:
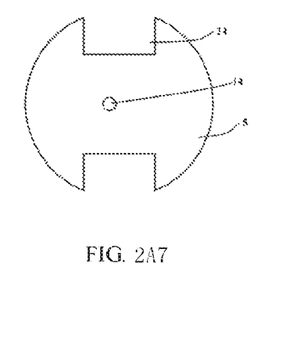
Figure 2A:
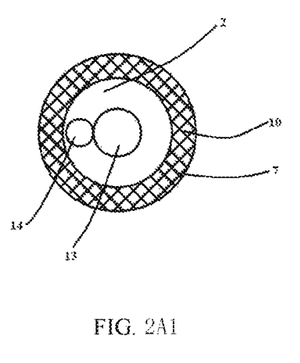
Figure 2A:
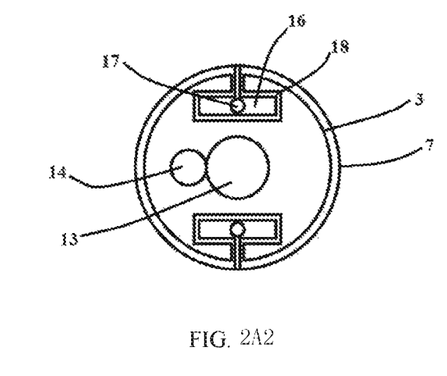
Figure 2A:
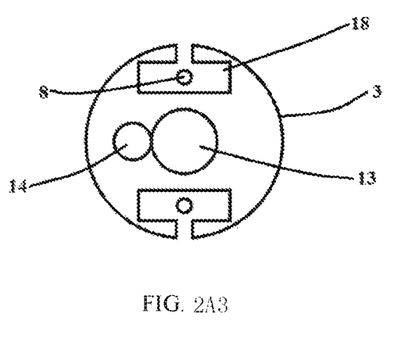
Figure 2A:
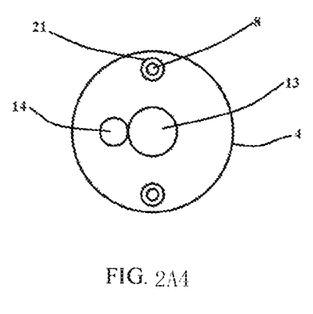
Figure 2A:
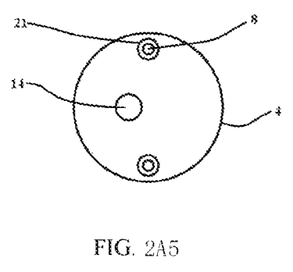
Figure 2A:
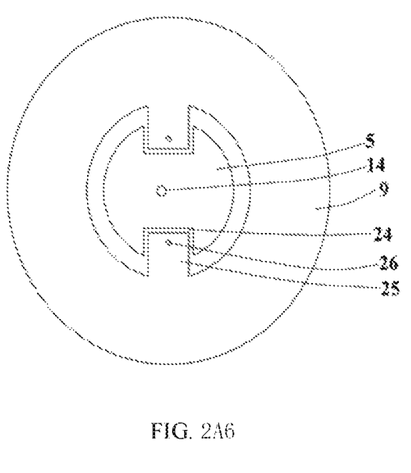
Figure 2B:
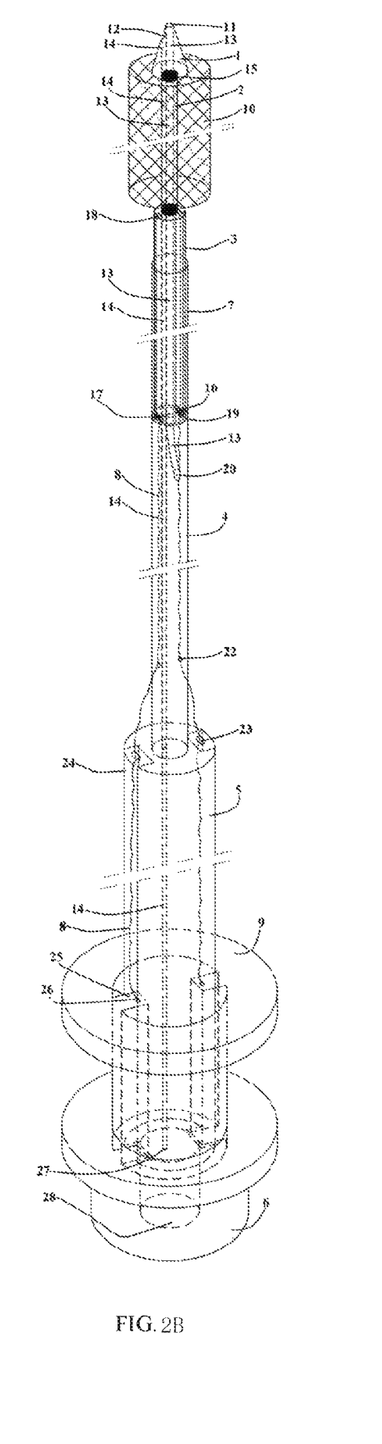
FIG. 2B is a structure diagram of the delivery device of an embodiment according to the present invention after the H-shaped is pulled back, the short sheath is moved back and the stent is deployed.
Figure 2B:
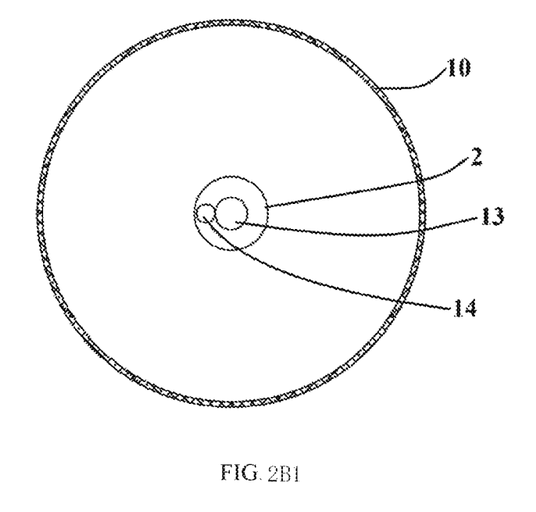
Figure 2B:
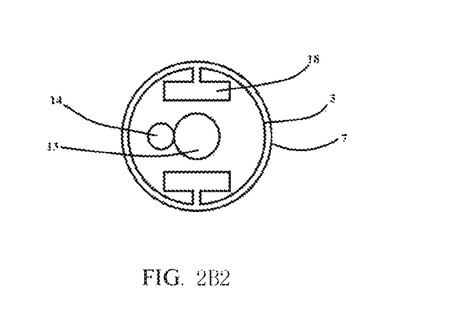

Please refer to FIG. 2A, FIG. 2A is a structure schematic of the stent of the delivery device of an embodiment according to the present invention before it is deployed; At the same time, please also refer to FIG. 2A1-FIG. 2A7, which is a cross-sectional view of each section of the delivery device of an embodiment according to the present invention before the stent is deployed.

FIG. 2A is a structure schematic diagram of an embodiment according to the present invention, before the stent of delivery device is deployed, which comprises, the tip 1, the inner rod 2, the stent 10, the short sheath 7, the connection thread 8, the secondary rod 3, the main rod 4, the sliding rod 5, the handle 9, and the trailing end 6. As shown in FIG. 2A, there are guidewire inlet 11 and injection tube outlet 12 at the top part of tip 1, which are connected to a guidewire cavity or cavity of guidewire 13 and injection tube 14 separately; wherein guidewire cavity 13 is a long cylindrical channel along the guidewire inlet 11 at the tip 1 to extend to the tail side and goes through the tip 1, inner rod 2, secondary rod 3, main rod 4 successively to the guidewire outlet 20 to be arranged on the main rod 4; and the guidewire outlet 20 is arranged on the tube wall nearby the top of the main rod 4, which is the intersection of the tube wall of the main rod 4 and the guidewire cavity 13 when the guidewire cavity 13 extends out from the main rod 4, and guidewire 42 piercing out from guidewire cavity 13 goes from guidewire inlet 11 through guidewire cavity 13 and come out guidewire outlet 20; injection tube 14 is arranged from injection tube outlet 12 at tip 1, through tip 1, inner rod 2, secondary rod 3, main rod 4, sliding rod 5, and to injection port 28, which can connect an external syringe needle, at the trailing end 6; the injection port 28 is applied to inject the contrast agent through the injection port 28, by which discharged from the injection tube outlet 12 the position of tip 1 can be located. the tail part of tip 1 is connected to inner rod 2, wherein inner rod 2 is arranged in the center of short sheath 7, and stent 10 is arranged in the cavity formed by inner rod 2 and short sheath 7; tip 1, inner rod 2, secondary rod 3 and main rod 4 are as one whole structure, and the external diameter of inner rod 2 is smaller than that of secondary rod 3, the external diameter of secondary rod 3 is smaller than that of main rod 4; the external diameter of main rod 4 is equal to or greater than that of short sheath 7; As shown in FIG. 2A1, is a cross-sectional view of the short sheath wrapping stent and inner rod, the cross section of guidewire cavity 13 and injection tube 14 can be seen on the section of inner rod 2; the external diameter of secondary rod 3 is smaller than that of main rod 4; the external diameter of secondary rod 3 is equal to or greater than that of short sheath 7. As shown in FIG. 2A2, is a cross-sectional view of the short sheath and the secondary rod of an embodiment according to the present invention before the stent of the delivery device is deployed, as shown FIG. 2A2, there is the T-shaped longitudinal sliding groove 18 to be arranged on two sides of secondary rod 3, and there is T-shaped buckle 16 to be arranged at the tail of the short sheath 7, and connection thread 8 is connected to the thread attachment point 17 of the T-shaped buckle 16 to be arranged at the tail part of T-shaped buckle 16; As shown in FIG. 2A3, is a cross-sectional view of secondary rod 3 which is not be sleeved to by short sheath 7, as shown in FIG. 2A3, the cross section of guidewire cavity or cavity of guidewire 13, injection tube 14, T-shaped longitudinal sliding groove 18, and connection thread 8 can be seen; In the embodiment, the external diameter of main rod 4 is equal to the external diameter of short sheath 7 to make short sheath 7 not continue moving along main rod 4 when short sheath 7 moves to the tail side, but move on secondary rod 3.

In another embodiment in the present invention, the external diameter of main rod 4 may be greater than that of short sheath 7; at boundary of main rod and secondary rod 19, T-shaped longitudinal sliding groove 18 at the tail part of secondary rod 3 is connection to the top part of connection thread tube 21 of main rod 4, to accommodate connection thread 8 to connect short sheath 7;

The connection thread 8 passes in turn through the T-shaped longitudinal sliding groove 18 on the two sides of an interior of the secondary rod 3 and connection thread tube 21 to be arranged in main rod 4, the cross-sectional view of connection thread tube 21's passing through main rod 4 is as shown in FIG. 2A4 (the section of the main rod with the guidewire cavity) and FIG. 2A5 (the section of the main rod without the guidewire cavity). As shown in FIG. 2A, FIG. 2A4, and FIG. 2A5, connection thread tube 21 extends to the tail part to the main rod thread outlet 22 at the side wall near the rear part of main rod 4, wherein the main rod thread outlet 22 is the intersection of connection thread tube 21 and main rod 4 extend; main rod 4 is connected to sliding rod 5, and the diameter of sliding rod 5 is greater than that of main rod 4; concave slideways 24 are arranged on two sides of sliding rod 5, and there is a thread passing hole 23 of the sliding rod 5 to be arranged at the top part of sliding rod 5; sliding rod 5 is wrapped around by the handle; there is convex protrusion 25 to be arranged on two sides of slideway to protrude to sliding rod 5 in the cavity of the center of the handle, and there is a thread attachment point 26 of the convex protrusion 25 at the top part of convex protrusion 25 to connect and fix connection thread 8 to pass through the main rod thread outlet 22 and main rod thread outlet, so as to drive short sheath 7 to slide along the secondary rod 3 when the handle 9 slides sliding rod 5, As shown in FIG. 2A6, is a cross-sectional view of the top part of the handle; the tail part of sliding rod 5 is connected to trailing end 6; the injection port 28 is arranged to the tail part of the rear end to connect to the syringes. injection port 28 is connected to injection tube 14 in sliding rod 5 through the handle 9; As shown in FIG. 2A6, is a cross-sectional view of the top part of the handle.

There are markers 15 which not penetrate the X-ray that being coating at the two ends of the inner rod 2, in one embodiment of the present invention, markers 15 which not penetrate the X-ray is X-ray impermeable coating metal markers to locate the locations of the inner rod 4 and the stent 7 by determining the mark location under X-ray. When the delivery device of the present invention is used, it can achieve single-handed and single-person operations: a thumb pressing against the trailing end 6, at least two fingers push two sides of the handle 9 respectively to slowly move close to the thumb, and the handle 9 shifts up on the slideway of sliding rod 5 so as to drive the short sheath 7 to move to secondary rod 3 by connection thread 8, therefore the stent 10 loses an external pressure around and expands to be deployed.

In the embodiment of the present invention, the short sheath can be designed to be slightly longer than the stent, and does not coat the main rod, this will not cause the influence of the shift of the stent and the inner rod when the stent is deployed, until the stent is deployed completely and accurately.

In one embodiment of the present invention, the sliding rod length is not less than that of the secondary rod.

Figure 3A:
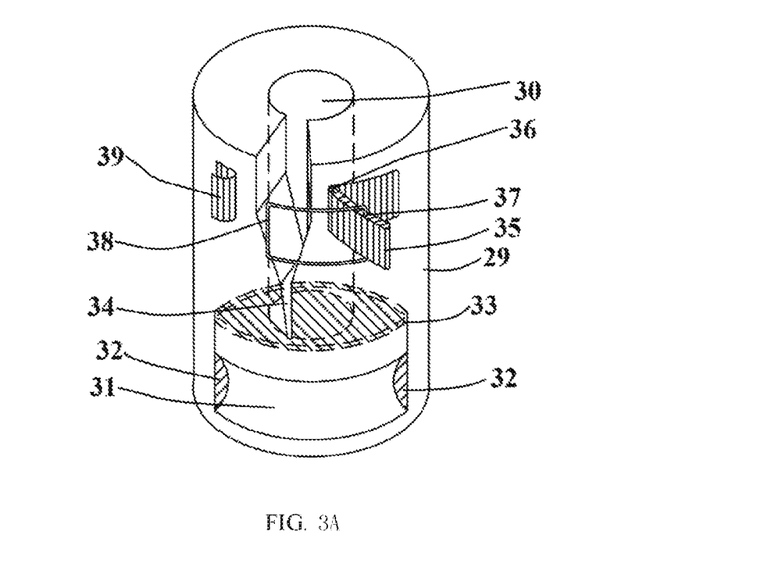
FIG. 3A is a schematic diagram of the fixing device of an embodiment according to the present invention at an unfixed state.
Figure 3B:
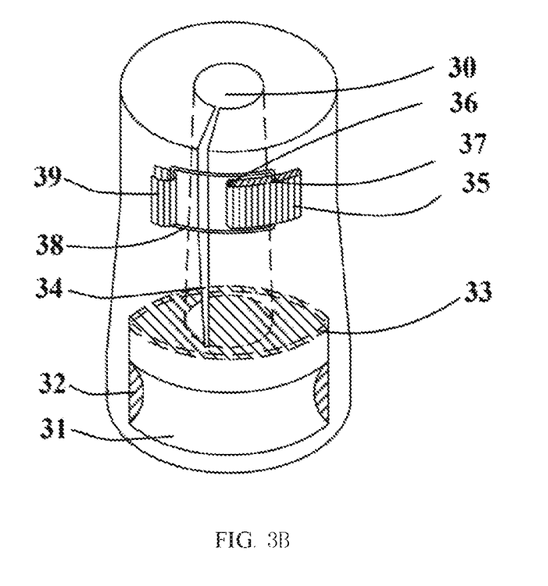
FIG. 3B is a schematic diagram of the fixing device of an embodiment according to the present invention at a fixed state.

Please refer to FIGS. 3A and 3B, FIGS. 3A and 3B is a schematic diagram of the fixing device of an embodiment of the present invention. The fixing device of a short sheath delivery system for a biliary metal stent via an endoscope comprises a fixing cap and a fixing latch.

Figure 4:
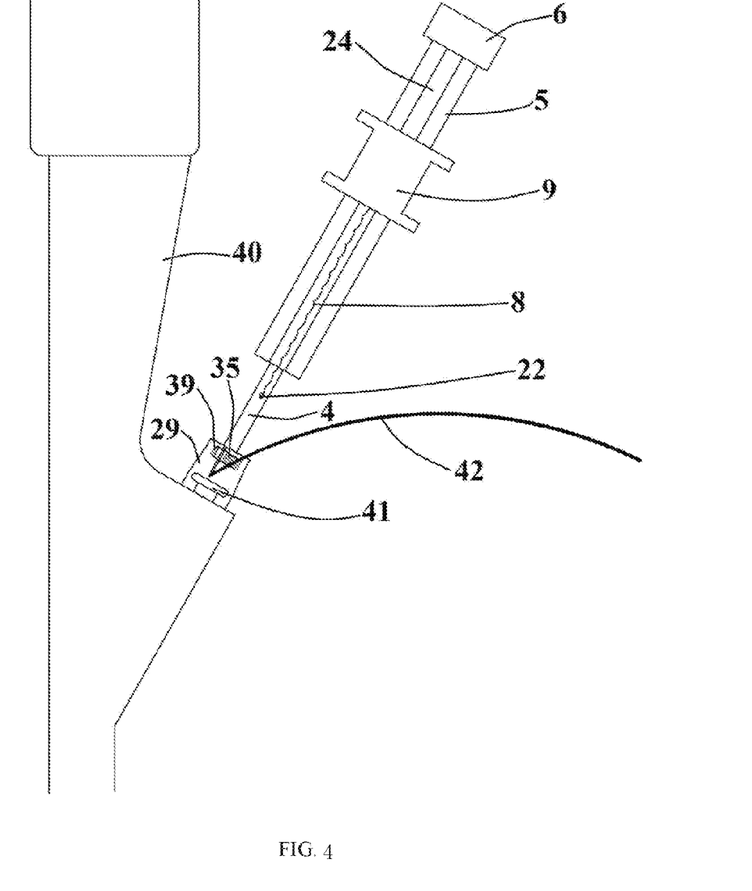
FIG. 4 is a schematic diagram of the delivery device and the guidewire of an embodiment according to the present invention, wherein the delivery device and the guidewire are fixed at the endoscope biopsy port by the fixed device.

In order to learn the fixing device shown in FIG. 3 specifically, please refer to FIG. 4, as shown in FIG. 4, which is a schematic diagram of fixing the main rod and the guidewire of the delivery device piercing into the delivery device at the endoscope biopsy port by the fixture of an embodiment according to the present invention.

As shown in FIG. 3A, is a structure diagram of the fixing cap 29 at an unfixed state, there is retractable biopsy channel 30 to be arranged at the center of fixing cap 29 so as to sleeve the delivery device on the endoscope biopsy port 41, as shown in FIG. 4; a thin adhesive film 33 to be arranged annularly in a middle part of the retractable biopsy channel so as to prevent gases and contents in the retractable biopsy channel 30 from counterflowing; and the thin adhesive film 33 may be punctured by relate instruments to let the guidewire 42 and the main rod 4 to pass through, the sealability of which is good; a wedge-shaped guidewire groove 34 is arranged longitudinally from the exterior of guidewire channel 34 to the top of the thin adhesive film 33 so as to fix guidewire 42 piercing out from the guidewire outlet, as shown in FIG. 4; a base groove 31 to connect the endoscope biopsy port and an annular rubber ring to clamp the endoscope biopsy port 41 are both arranged at the bottom of the fixing cap 29; the fixing latch includes U-shaped groove 39, pulling latch 35 and latch ring 38, wherein U-shaped groove 39 and pulling latch 35 are fixed on both sides of guidewire groove 34, pulling latch 35 can be turned over by main shaft 36, latch ring 38 is a rectangular hollow ring, wherein one side of the latch ring 38 is embedded in side shaft holes 37 of two sides of the pulling latch 35 and can turn over along with the shaft; As shown in FIG. 3B, is a structure diagram of the fixing cap at a fixed state, after latch ring 38 is turned off to buckle U-shape groove 39, pulling latch 35 may be pulled to clamp the fixing latch tightly, therefore the retractable channel 30 retracts to fix the main rod 4, as shown in FIG. 4, While putting into practice, first base groove 31 of fixing cap 29 biopsy is buckled on endoscope biopsy port 41, an annular rubber ring 32 is annularly arranged around the base groove 31 to guarantee closing the fixing cap 29 and the endoscope biopsy port 41 fasten, therefore endoscope biopsy port 41 is firmly embedded into base groove 31. Further, the location of the biliary passage is determined for the stent to be placed by endoscope 40, the top part of guidewire 42 is inserted into through retractable biopsy channel 30 of fixing cap 29, guidewire 42 pierces the thin adhesive film 33 and enters into the endoscope biopsy port 41, continues to insert guidewire 42 along the endoscopic biopsy channel, until it passes over the location of the biliary passage where the stent is placed. The trailing end of guidewire 42 is inserted into guidewire inlet 11, guidewire 42 passes through tip 1, inner rod 2, and secondary rod 3 along guidewire cavity 13, and pierce out from guidewire outlet 20 of the side wall of main rod 4. Further along guidewire 42 tip 1 is sent into retractable biopsy channel 30 of fixing cap 29, until the fore part of guidewire outlet 20 of guidewire 4 completely enters into retractable biopsy channel 30, so far the unveiled part of guidewire 42 in retractable biopsy channel 30 stays paralleling in retractable biopsy channel 30. The unveiled guidewire 42 in retractable biopsy channel 30 is embedded in guidewire channel 34 of the side of fixing cap 29 to be fixed, in order to prevent the guidewire 42 from moving during pushing the stent.

Further, the position of short sheath 7 were observed under the endoscope, when the position of X-ray opaque marker of two ends of inner rod 2 is observed in the X-ray, inner rod 2 and stent 10 are adjusted to the target position for the stent to be placed, in the mean time, the contrast agent can be injected into through injection port 28, the contrast agent is discharged from injection tube outlet 12 through injection tube 14 to locate the position of the tip 1, so inner rod 2 and stent 10 are adjusted to be placed the target position of the stent.

A latch ring 38 and a pulling latch 35 of the buckle of the fixing device is turned over to make latch ring 38 buckle U-shape groove 39, then pulling latch 35 is pulled back to clamp the fixing latch tight, the locked state shown after the fixing latch is fixed in FIG. 3B, and therefore the retractable channel 30 retracts to fix the main rod 4.

Further, after the fixing device is fixed to endoscope biopsy port 41 and to fix delivery device and the guidewire by the fixing device, the operator presses against the trailing end by one thumb, and infibulates the handle 9 by his/her forefinger and middle finger to draw it back slowly, the handle 9 moves the slideway of sliding rod 5, the thread attachment point 26 on the top part of convex protrusion 25 draws the connection thread 8, wherein connection thread 8 drives the T-shaped buckle 16 of short sheath 7 to move back along T-shaped longitudinal sliding groove 18 arranged on two sides of an interior of the secondary rod 3, to make short sheath 7 off the location that stent stays slowly, and cover secondary rod 3 the external diameter of short sheath is less than the internal diameter of which. The stent 10 begins to self-expand after stent 10 loses the control by short sheath 7. When the tail part of short sheath 7 moves to the placement of boundary of the main rod and the secondary rod 19, it will meet main rod 4, its external diameter is equal to or bigger than that of main rod 4, it can not move up for the impediment, the operator will stop pulling up the handle. At this time, short sheath 7 is completely out of stent 10 and completely arranged in secondary rod 3, stent 10 loses its cover of short sheath 7 to expand and be fully deployed in the target position.

In one embodiment of the present invention, connection thread 8 and T-shaped buckle 16 at the tail part of short sheath 7 are fitting tightly, and it is requested to ensure the pull process operate smoothly and do not break in T-shaped longitudinal sliding groove 18 of two sides of an interior of the secondary rod 3, and passing through secondary rod 3 and main rod 4 in connection thread tube 21 in main rod 4, connection thread 8 passing through the main rod thread outlet 22 and thread passing hole 23 of sliding rod and fitting tightly on the thread attachment point 26 of the convex protrusion 25 of the handle 9. The lengths of sliding rod 5 of the delivery device and secondary rod all are little longer than that of short sheath 7, so it can ensures that short sheath 7 has sufficient stroke to move back to take off the position of stent 10, to ensure stent 10 to be completely deployed.

In the embodiment, the external diameter of short sheath 7 is equal to the external diameter of main rod 4, when short sheath 7 moves back along secondary rod 3 to boundary of main rod and secondary rod 19, it will be locked, and will not sleeve out of main rod 4.

After the successful deploy of the stent, fixing cap 29 forces to be pulled out, when guidewire 42 and delivery device are withdrawn together at the same time from the endoscope biopsy port to end the whole stent pushing process.

It would be appreciated by those skilled in the art that: the drawings are schematic of an embodiment, the modules or processes in the accompanying drawings are not necessarily essential to implement the present invention.

It would be appreciated by those skilled in the art that: in the embodiment of the apparatus according to the embodiment of the module and according to the distribution apparatus in the embodiment described, the corresponding changes can also be located in one embodiment of the present embodiment differs from the one or more devices. The module of the above embodiment can be combined into one module may be further split into a plurality of submodules.

Finally, it should be noted that: the above embodiments are merely to illustrate the technical aspect of the present invention, but not intended to limit; despite the reference to the aforementioned embodiments of the present invention has been described in detail, those skilled in the art should understand: it is still possible that the technical solution described in the foregoing embodiment is modified, or some technical features are replaced in equivalent; when these modifications or replacements do not essentially corresponding technical solutions departing from the spirit and scope of the invention to implement technical solutions.

What is claimed is:

1. A short sheath delivery system for a biliary metal stent via an endoscope,
   the delivery system comprising a tip, an inner rod, a secondary rod, a main rod, a sliding rod and a trailing end, a short sheath, a handle and a stent, wherein the short sheath and the handle are connected by a connection thread, and the stent is arranged around the inner rod, wherein,
   a guidewire inlet and an injection tube outlet exist on a top of the tip;
   the tip, the inner rod, the secondary rod and the main rod are integrated, and an external diameter of the inner rod is less than an external diameter of the secondary rod, and the external diameter of the secondary rod is less than an external diameter of the main rod;
   the short sheath covers around the inner rod, and an empty cavity is formed between the short sheath and the inner rod to contain the stent in the empty cavity before the stent is deployed;
   the length of the short sheath is greater than that of the stent, and is less than that of the secondary rod;
   the external diameter of the secondary rod is less than an inner diameter of the short sheath, and T-shaped longitudinal sliding grooves are arranged on two sides of an interior of the secondary rod, and T-shaped buckles are arranged at a tail of the short sheath and are embedded in the T-shaped longitudinal sliding grooves, wherein a first end of the connection thread is connected with a thread attachment point of the T-shaped buckle, wherein the thread attachment point of the T-shaped buckle is arranged on one of the T-shaped buckles;
   the external diameter of the main rod is equal to or greater than that of the short sheath;
   a long cylindrical channel extends from the guidewire inlet arranged at the tip to the trailing end and goes successively through the tip, the inner rod, the secondary rod, and the main rod to a guidewire outlet arranged on the main rod, wherein the long cylindrical channel is a guidewire cavity; and the guidewire outlet is arranged on a side wall of the main rod, and the guidewire outlet is an intersection point of a tube wall of the main rod and the guidewire cavity when the guidewire cavity extends out from the main rod;

the external diameter of the sliding rod is greater than the external diameter of the main rod; concave slideways are arranged on two sides of the sliding rod, and the handle is sleeved around the sliding rod; and convex protrusions are arranged on inner sides of the handle and protrude to concave sides of the concave slideways so as to slide the handle along the sliding rod; thread attachment points of the convex protrusions are arranged on a top of the convex protrusions so as to be connected with a second end of the connection thread;

the connection thread starts at the T-shaped buckles arranged at a tail part of the short sheath, successively passes through the T-shaped longitudinal sliding grooves which are arranged on the two sides of the interior of the secondary rod, through a connection thread tube which is arranged in the main rod, then through a main rod thread outlet which is arranged on the tube wall at a tail part of the main rod, and through a thread passing hole of the sliding rod which is arranged on a top of the sliding rod, and finally connects to the thread attachment points of the convex protrusions, therefore the connection thread drives the short sheath to slide along the secondary rod towards the trailing end when the handle slides along the sliding rod to the trailing end;

an injection port is arranged at the trailing end so as to be externally connected with a syringe needle;

an injection tube is arranged from the injection tube outlet which is located at the tip, through the tip, the inner rod, the secondary rod, the main rod, the sliding rod, and to the injection port which is located at the trailing end; the injection tube is used for injecting a contrast agent through the injection port, so as to locate the position of the tip by discharging the contrast agent from the injection tube outlet.

2. The short sheath delivery device for delivering the metal stent in the biliary tract via an endoscope as claimed in the claim 1, wherein, the length of the sliding rod is not less than that of the secondary rod.

3. The short sheath delivery device for delivering the metal stent in the biliary tract via an endoscope as claimed in the claim 1, wherein, X-ray opaque markers are coated at two ends of the inner rod to locate positions of the inner rod and the stent by X-ray.

4. A short sheath delivery system for delivering a metal stent in a biliary tract via an endoscope, wherein, the delivery system comprises the delivery device as in claim 1 and a fixing device; wherein, the fixing device is used for connecting an endoscope biopsy port and fixing the main rod and the guidewire, the fixing device including a fixing cap and a fixing latch, wherein, a retractable biopsy channel is arranged at the center of fixing cap so as to sleeve the delivery device on the endoscope biopsy port; a thin adhesive film is arranged annuarly in a middle part of the retractable biopsy channel, and the thin adhesive film has good resilience and sealability so as to prevent gases and contents in the retractable biopsy channel from counterflowing; and the thin adhesive film is configured to be punctured in a middle part of the thin adhesive film when the main rod and the guidewire of the delivery device pass through the retractable biopsy channel; a wedge-shaped guidewire groove is arranged longitudinally from an exterior of the pass channel to the top of the thin adhesive film so as to fix the guidewire piercing out from the guidewire outlet; a base groove to connect the endoscope biopsy port and an annular rubber ring to clamp the endoscope biopsy port are both arranged at the bottom of the fixing cap;

the fixing latch includes a U-shaped groove, a pulling latch and a latch ring, wherein the U-shaped groove and the pulling latch are respectively fixed on two sides of the guidewire groove, and the pulling latch can be turned over by the main shaft, the latch ring is a rectangular hollow ring, wherein one side of the latch ring is embedded in side shaft holes of two sides of the pulling latch and drives the pulling latch to turn over along with the main shaft, and turn over the pulling latch and the latch ring so as to turn over the pulling latch back to clamp the fixing latch tightly after the latch ring latches the U-shaped groove, therefore the retractable channel retracts to fix the main rod and to press and fix the guidewire tightly by the guidewire groove.

5. The short sheath delivery system for delivering the metal stent in the biliary tract via an endoscope as claimed in the claim 4, wherein the fixing latch and the fixing cap are integrated.

6. A single-handed operating method of the short sheath delivery device for delivering the metal stent in the biliary tract via the endoscope as claimed in the claim 1, the method comprising: pressing a thumb against the trailing end, pulling two sides of the handle respectively with at least two fingers to slowly move close to the thumb, and driving the short sheath with the handle to move over the secondary rod by the connection thread, therefore the stent loses an external pressure around and expands to be deployed.

7. A single-handed operating method of the short sheath delivery system for delivering the metal stent in the biliary tract via the endoscope as claimed in the claim 4, the method comprising: pressing a thumb against the trailing end, pulling two sides of the handle respectively with at least two fingers to slowly move close to the thumb, and driving the short sheath with the handle to move over the secondary rod by the connection thread, therefore the stent lose an external pressure around and expands to be deployed.

* * * * *